United States Patent
Sauer et al.

(10) Patent No.: US 9,888,968 B2
(45) Date of Patent: Feb. 13, 2018

(54) METHOD AND SYSTEM FOR AUTOMATED THERAPY PLANNING FOR ARTERIAL STENOSIS

(71) Applicant: Siemens Healthcare GmbH, Erlangen (DE)

(72) Inventors: Frank Sauer, Princeton, NJ (US); Puneet Sharma, Monmouth Junction, NJ (US); Max Schoebinger, Hirschaid (DE)

(73) Assignee: Siemens Healthcare GmbH, Erlangen (DE)

( * ) Notice: Subject to any disclaimer, the term of this patent is extended or adjusted under 35 U.S.C. 154(b) by 294 days.

(21) Appl. No.: 14/801,987

(22) Filed: Jul. 17, 2015

(65) Prior Publication Data

US 2016/0022371 A1    Jan. 28, 2016

Related U.S. Application Data

(60) Provisional application No. 62/027,347, filed on Jul. 22, 2014.

(51) Int. Cl.
*G06K 9/00* (2006.01)
*A61B 19/00* (2006.01)
(Continued)

(52) U.S. Cl.
CPC .............. *A61B 19/50* (2013.01); *A61B 6/032* (2013.01); *A61B 6/481* (2013.01); *A61B 6/504* (2013.01);
(Continued)

(58) Field of Classification Search
CPC .......... A61B 19/50; A61B 6/481; A61B 6/032; A61B 6/5217; A61B 6/463; A61B 6/466;
(Continued)

(56) References Cited

U.S. PATENT DOCUMENTS

| | | | |
|---|---|---|---|
| 6,236,878 B1 | 5/2001 | Taylor et al. | |
| 7,860,290 B2 | 12/2010 | Gulsun et al. | |

(Continued)

FOREIGN PATENT DOCUMENTS

| | | |
|---|---|---|
| CN | 102346811 A | 2/2012 |
| CN | 103270513 A | 8/2013 |

(Continued)

OTHER PUBLICATIONS

C.A. Taylor, et al., "Open Problems in Computational Vascular Biomechanics: Hemodynamics and Arterial Wall Mechanics," Comput Methods Appl Mech. Eng., vol. 198, pp. 3514-3523, 2009.
(Continued)

*Primary Examiner* — John Strege (57) ABSTRACT

A method and system for automated decision support for treatment planning of arterial stenoses is disclosed. A set of stenotic lesions is identified in a patient's coronary arteries from medical image data of the patient. A plurality of treatment options are generated for the set of stenotic lesions, wherein each of the plurality of treatment options corresponds to a stenting configuration in which one or more of the stenotic lesions are stented. For each of the plurality of treatment options, predicted hemodynamic metrics for the set of stenotic lesions resulting from the stenting configuration corresponding to that treatment option are calculated.

33 Claims, 8 Drawing Sheets

(51) Int. Cl.
*G06F 19/00* (2018.01)
*G06T 7/00* (2017.01)
*G06T 7/20* (2017.01)
*G06T 11/20* (2006.01)
*A61B 6/00* (2006.01)
*A61B 6/03* (2006.01)

(52) U.S. Cl.
CPC .......... *G06F 19/321* (2013.01); *G06F 19/345* (2013.01); *G06T 7/0012* (2013.01); *G06T 7/20* (2013.01); *G06T 11/20* (2013.01); *A61B 6/463* (2013.01); *A61B 6/466* (2013.01); *A61B 6/5217* (2013.01); *G06T 2207/10088* (2013.01); *G06T 2207/30104* (2013.01)

(58) Field of Classification Search
CPC ......... A61B 6/504; G06T 7/0012; G06T 7/20; G06T 2207/30104; G06T 2207/10088; G06F 19/345; G06F 19/321
See application file for complete search history.

(56) References Cited

U.S. PATENT DOCUMENTS

| | | |
|---|---|---|
| 7,953,266 B2 | 5/2011 | Gulsun et al. |
| 8,098,918 B2 | 1/2012 | Zheng et al. |
| 8,157,742 B2 | 4/2012 | Taylor |
| 8,200,466 B2 | 6/2012 | Spilker et al. |
| 8,249,815 B2 | 8/2012 | Taylor |
| 8,311,747 B2 | 11/2012 | Taylor |
| 8,311,748 B2 | 11/2012 | Taylor et al. |
| 8,311,750 B2 | 11/2012 | Taylor |
| 8,315,812 B2 | 11/2012 | Taylor |
| 8,315,813 B2 | 11/2012 | Taylor et al. |
| 8,315,814 B2 | 11/2012 | Taylor et al. |
| 8,321,150 B2 | 11/2012 | Taylor |
| 8,386,188 B2 | 2/2013 | Taylor et al. |
| 8,682,626 B2 | 3/2014 | Ionasec et al. |
| 9,743,835 B2 | 8/2017 | Taylor |
| 2002/0118869 A1* | 8/2002 | Knoplioch ................ G06T 7/60 382/131 |
| 2007/0024617 A1* | 2/2007 | Poole ........................ G06T 7/60 345/424 |
| 2008/0069419 A1* | 3/2008 | Farag .................. G06F 19/3437 382/131 |
| 2008/0212857 A1* | 9/2008 | Pfister ................ A61B 5/02007 382/130 |
| 2009/0088830 A1* | 4/2009 | Mohamed ................ A61F 2/91 623/1.11 |
| 2010/0017171 A1 | 1/2010 | Spilker et al. |
| 2010/0067760 A1 | 3/2010 | Zhang et al. |
| 2011/0224542 A1* | 9/2011 | Mittal .................. G06T 7/0016 600/425 |
| 2012/0022843 A1* | 1/2012 | Ionasec ................ G06T 13/20 703/9 |
| 2012/0041301 A1 | 2/2012 | Redel |
| 2012/0041318 A1 | 2/2012 | Taylor |
| 2012/0041319 A1 | 2/2012 | Taylor et al. |
| 2012/0041320 A1 | 2/2012 | Taylor |
| 2012/0041321 A1 | 2/2012 | Taylor et al. |
| 2012/0041322 A1 | 2/2012 | Taylor et al. |
| 2012/0041323 A1 | 2/2012 | Taylor et al. |
| 2012/0041324 A1 | 2/2012 | Taylor et al. |
| 2012/0041735 A1 | 2/2012 | Taylor |
| 2012/0041739 A1 | 2/2012 | Taylor |
| 2012/0053918 A1 | 3/2012 | Taylor |
| 2012/0053919 A1 | 3/2012 | Taylor |
| 2012/0053921 A1 | 3/2012 | Taylor |
| 2012/0059246 A1 | 3/2012 | Taylor |
| 2012/0072190 A1 | 3/2012 | Sharma et al. |
| 2012/0121151 A1 | 5/2012 | Bernhardt et al. |
| 2012/0150516 A1 | 6/2012 | Taylor et al. |
| 2012/0203530 A1 | 8/2012 | Sharma et al. |
| 2012/0243761 A1 | 9/2012 | Senzig et al. |
| 2013/0054214 A1 | 2/2013 | Taylor |
| 2013/0064438 A1 | 3/2013 | Taylor et al. |
| 2013/0132054 A1* | 5/2013 | Sharma ................ G06F 19/12 703/9 |
| 2013/0246034 A1 | 9/2013 | Sharma et al. |
| 2014/0058715 A1 | 2/2014 | Sharma et al. |
| 2014/0200867 A1 | 7/2014 | Lavi et al. |
| 2015/0092999 A1* | 4/2015 | Schmitt .................. A61B 5/742 382/128 |
| 2015/0112182 A1 | 4/2015 | Sharma et al. |

FOREIGN PATENT DOCUMENTS

| | | |
|---|---|---|
| CN | 103300820 A | 9/2013 |
| WO | WO2013071219 | 5/2013 |

OTHER PUBLICATIONS

Chamuleau et al., "Association between coronary lesion severity and distal microvascular resistance in patients with coronary artery disease," Am J Physiol Heart Circ Physiol, vol. 285, pp. H2194-H2200, 2003.

De Bruyne et al., "Simultaneous Coronary Pressure and Flow Velocity Measurements in Humans," Circulation, vol. 94, pp. 1842-1849, 1996.

H. Vernon Anderson et al., "Coronary Atery Flow Velocity is Related to Lumen Area and Regional Left Ventricular Mass," Circulation, vol. 102, pp. 48-54, 2000.

Chinese Office Action dated Sep. 5, 2017 in corresponding Chinese application No. 201510602460.6.

* cited by examiner

METHOD AND SYSTEM FOR AUTOMATED THERAPY PLANNING FOR ARTERIAL STENOSIS

This application claims the benefit of U.S. Provisional Application No. 62/027,347, filed Jul. 22, 2014, the disclosure of which is herein incorporated by reference.

BACKGROUND OF THE INVENTION

The present invention relates to treatment planning for arterial stenosis, and more particularly, to selecting which stenoses or lesions to stent based on medical image data of a patient.

Cardiovascular disease (CVD) is the leading cause of deaths worldwide. Among various CVDs, coronary artery disease (CAD) accounts for nearly fifty percent of those deaths. Local narrowing of a blood vessels, or stenosis, represents an important cause of cardiovascular diseases. Such stenoses typically develop gradually over time, and can develop in different parts of the arterial circulation, such as the coronary arteries, renal arteries, peripheral arteries, carotid artery, cerebral artery, etc. Such a local narrowing can also be the result of a congenital defect. One therapy widely used for treating arterial stenosis is stenting, i.e., the placement of a metal or polymer stent in the artery to open up the lumen, and hence facilitate the flow of blood. When dealing with coronary artery stenosis, the stenting therapy is referred to as percutaneous coronary intervention (PCI).

In recent years, there has been considerable focus on computational approaches for modeling the flow of blood in the human cardiovascular system. When used in conjunction with patient-specific anatomical models extracted from medical images, such computational techniques can provide important insights into the structure and function of the cardiovascular system.

BRIEF SUMMARY OF THE INVENTION

The present invention provides a method and system for automated decision support for therapy planning for arterial stenoses or lesions based on medical image data. Embodiments of the present invention acquire medical image data of a patient's heart, segment the medical image data and extract a geometrical model of the coronary arteries, and utilize computational techniques to compute hemodynamic quantities for various stenoses in the patient's coronary arteries. Embodiments of the present invention identify a set of possible treatment options, each corresponding to a possible combination of stents covering one or multiple stenoses, and calculate computational hemodynamic quantities for each of the treatment options. Embodiments of the present invention generate a clinically relevant figure of merit for each of the treatment options and present the results to a user to provide decision support for selecting one of the treatment options.

In one embodiment of the present invention, a set of stenotic lesions is identified in a patient's coronary arteries from medical image data of the patient. A plurality of treatment options are generated for the set of stenotic lesions, wherein each of the plurality of treatment options corresponds to a stenting configuration in which one or more of the stenotic lesions are stented. For each of the plurality of treatment options, predicted hemodynamic metrics for the set of stenotic lesions resulting from the stenting configuration corresponding to that treatment option are calculated.

These and other advantages of the invention will be apparent to those of ordinary skill in the art by reference to the following detailed description and the accompanying drawings.

DETAILED DESCRIPTION

The present invention relates to a method and system for automated decision support for treatment planning of arterial stenosis. Embodiments of the present invention are described herein to give a visual understanding of the methods for treatment planning for arterial stenosis. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Medical image data of a patient's heart, such as computed tomography (CT) data can be acquired and used to extract quantitative information that supports the choice between different therapy options for coronary artery stenoses. The medical image data can be segmented to extract a model of the patient's coronary arteries. The pressure drop values across a plurality of stenotic lesions can be computed non-invasively, for example using computational fluid dynamics (CFD) or other computational approaches such as machine-learning based approaches, and these values can be used to compute hemodynamic quantities, such as fractional flow reserve (FFR), that support an initial clinical decision regarding whether or not therapy in the form of stenting one or more of the lesions is needed. It is then desirable to provide the clinician with further quantitative information that supports the choice of how many lesions to stent and which lesions to stent. As stenting one lesion changes the blood flow in the corresponding artery (and to a much lesser extent, the blood flow in the other main coronary arteries) and hence the pressure drop values across other lesions that are located upstream or downstream in the same coronary artery, it is desirable to generate quantitative information that would automatically suggest the optimal stent configuration for treating the patient's stenotic lesions.

Embodiments of the present invention are described herein for providing automated decision support for percutaneous coronary intervention (PCI) treatment planning for stenting coronary artery stenoses (lesions). However, it is to be understood that the methods described herein can be similarly applied for treatment planning for stenting stenotic lesions in other types of arteries as well, such as the renal arteries, peripheral arteries, carotid artery, cerebral artery, etc. The methods described herein can also be applied to other parts of the circulatory system, such as for venous circulation or pulmonary circulation. Embodiments of the present invention can also be applied to treatment planning for airways.

Figure 1:
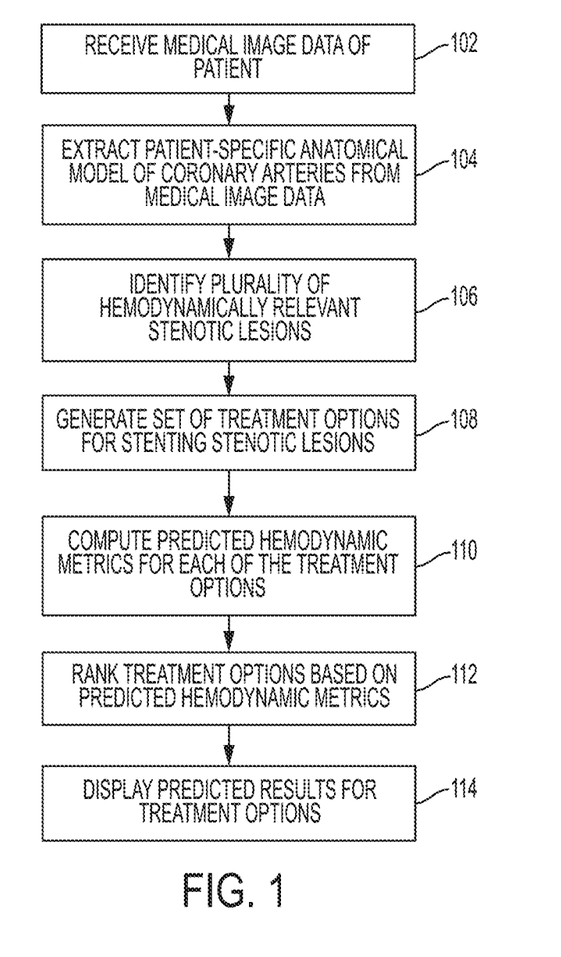
FIG. 1 illustrates a method of treatment planning for a plurality of coronary artery stenotic lesions of a patient according to an embodiment of the present invention.

FIG. 1 illustrates a method of treatment planning for a plurality of coronary artery stenotic lesions of a patient according to an embodiment of the present invention. Referring to FIG. 1, at step 102, medical image data of a patient is received. The medical image data is acquired prior to performing stenting, such as PCI for a coronary artery stenosis. Medical image data from one or multiple imaging modalities can be received. For example, the medical image data can include, computed tomography (CT), Dyna CT, magnetic resonance (MR), Angiography, Ultrasound, Single Photon Emission computed Tomography (SPECT), and any other type of medical imaging modality. The medical image data can be 2D, 3D, or 4D (3D+time) medical image data. The medical image data can be received directly from one or more image acquisition devices, such as a CT scanner, MR scanner, Angiography scanner, Ultrasound device, etc., or the medical image data may be received by loading previously stored medical image data for a patient.

In an advantageous embodiment, 3D coronary CT angiography (CTA) images are acquired on a CT scanner. The CTA images ensure that the coronary vasculature, including the vessel(s) that contain the stenosis, is adequately imaged using a contrast agent that is injected into the patient. At this stage, the clinician may be provided with an option of identifying lesions (stenoses) of interest by interactively viewing them on the images. This step can also be performed on a patient-specific anatomical model that is extracted from the image data (step 104). Alternatively, the stenoses may be automatically detected in the image data using an algorithm for automatic detection of coronary artery stenosis, such as the method for automatic detection of coronary artery stenosis described in United States Published Patent Application No. 2011/0224542, which is incorporated herein by reference. In addition to the medical image data, other non-invasive clinical measurements, such as the patient's heart rate and systolic and diastolic blood pressure may also be acquired. These non-invasive clinical measurements can be used to establish boundary conditions for CFD computations.

At step 104, a patient-specific anatomical model of the coronary arteries is extracted from the medical image data. The patient-specific anatomical model may be a patient-specific anatomical model of any portion of the full coronary artery tree of the patient. In order to generate the patient-specific anatomical model of the coronary artery tree, the coronary arteries can be segmented in the 3D medical image data using an automated coronary artery centerline extraction algorithm. For example, the coronary arteries can be segmented in a CT volume using the method described United States Published Patent Application No. 2010/0067760, which is incorporated herein by reference. Once a coronary artery centerline tree is extracted, cross-section contours can be generated at each point of the centerline tree. The cross-section contour at each centerline point gives a corresponding cross-section area measurement at that point in the coronary artery. A geometric surface model is then generated for the segmented coronary arteries. For example, methods for anatomical modeling of the coronary arteries are described in U.S. Pat. No. 7,860,290 and U.S. Pat. No. 7,953,266, both of which are incorporated herein by reference. In addition to the coronaries, the patient-specific anatomical model can include the aortic root together with the proximal part of the aorta. A detailed 3D model of each stenosis can also be extracted using similar algorithms, which includes the quantification of the proximal vessel diameter and area, distal vessel diameter and area, minimal lumen diameter and area, and length of stenosis.

Figure 2:
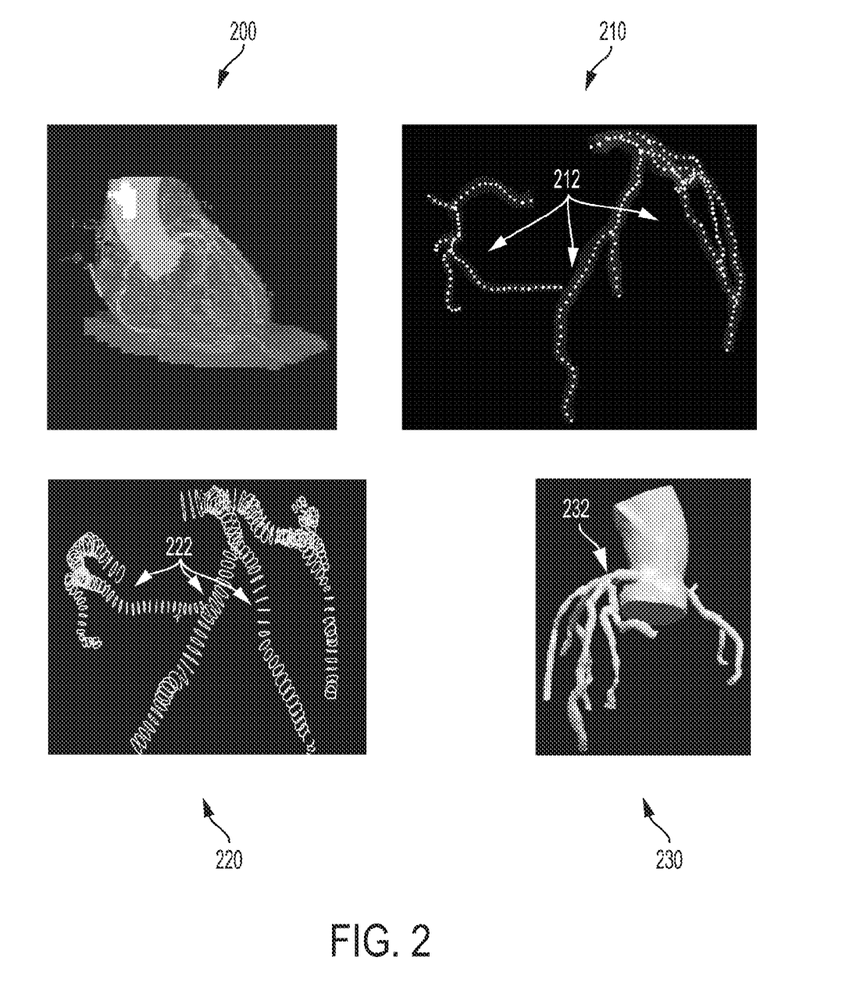
FIG. 2 illustrates exemplary results for generating a patient-specific anatomical model of the coronary vessel tree.

FIG. 2 illustrates exemplary results for generating a patient-specific anatomical model of the coronary vessel tree. Image 200 of FIG. 2 shows coronary CTA data. Image 210 shows a centerline tree 212 extracted from the CTA data. Image 220 shows a cross-section contours 222 extracted at each point of the centerline tree 212. Image 230 shows a 2D surface mesh 232 of the coronary arteries, the aortic root, and the proximal part of the aorta. It is to be understood that the anatomical model of the coronary tree of the patient can be output and displayed, for example on a display screen of the computer system.

The above described anatomical modeling tasks can be performed automatically or can be user-driven, thereby allowing the user (clinician) to interactively make changes to the anatomical models to analyze the effects of such changes on the subsequent computation of FFR. In addition to the coronary vessel tree, the myocardium may also be segmented (either automatically or manually) in the medical image data to determine an estimate of the left ventricular mass, which in a possible implementation, may be used to estimate the absolute resting flow for the patient which is used to calculate boundary conditions for a computational blood flow and pressure simulation. Alternatively, the resting flow could also be computed based on the total volume of the segmented coronary tree, or from the outlet radius of the different coronary vessels. In an exemplary embodiment, a patient-specific anatomical model of the heart that is automatically generated from the image data may be used for this purpose. The anatomical heart model is a multi-component model having multiple cardiac components, including the four chambers (left ventricle, left atrium, right ventricle, and right atrium). The anatomical heart model may also include components such as the heart valves (aortic valve, mitral valve, tricuspid valve, and pulmonary valve) and the aorta. Such a comprehensive model of the heart is used to capture a large variety of morphological, functional, and pathological variations. A modular and hierarchical approach can be used to reduce anatomical complexity and facilitate an effective and flexible estimation of individual anatomies. The 4D anatomical heart model can be generated by generating individual models of each heart component, for example using marginal space learning (MSL), and then integrating the heart component models by establishing mesh point correspondence. Additional details regarding generation of such a 4D patient-specific heart model are described in United States Published Patent Application No. 2012/0022843, which is incorporated herein by reference in its entirety.

At step 106, a plurality of hemodynamically relevant stenotic lesions are identified in the coronary artery. In order to identify the hemodynamically relevant stenotic lesions, all of the lesions can be automatically detected in the medical image data or in the patient-specific anatomical model of the coronary arteries and then a hemodynamic metric, such as FFR, can be computed for each of the detected lesions. Stenosis locations in the coronary tree can be automatically determined by performing coronary centerline extraction from the medical image data, calculating the vessel diameter in cross-sections along the centerline, and comparing the sequences of diameters. A stenosis (lesion) is detected wherever the diameter shrinks in the distal direction and then increases again. Additional details regarding a method for automatic detection of coronary artery stenosis are described in United States Published Patent Application No. 2011/0224542, which is incorporated herein by reference.

In an exemplary embodiment, FFR can be automatically calculated for each detected stenosis location by simulating blood flow and pressure in the patient-specific anatomical model of the coronary arteries using a computational model of coronary circulation. The blood flow and pressure can be simulated in the anatomical model using CFD computations or any other standard numerical technique, such as finite-element method, finite-difference method, finite volume method, boundary element method, embedded boundary method, immersed boundary method lattice Boltzmann method, etc. According to an advantageous embodiment of the present invention, a multi-scale computational model of coronary circulation can be used to compute the compute the blood flow and pressure in the pre-stenting anatomical model of the coronary arteries over a series of time steps. For example, the simulation may be performed for a plurality of time steps corresponding to a fully cardiac cycle or multiple cardiac cycles. In a possible implementation, the computational model of coronary circulation can model the loss of pressure across stenoses or other narrowings in the coronary arteries (e.g., calcification, thrombus, bifurcation, etc.) using pressure-drop models. It is to be understood that throughout this disclosure, the terms stenosis and lesion are used to generally refer to any type of narrowing in a vessel. The pressure drop model for a particular stenosis computes the pressure drop over the stenosis due the narrowing of the vessel without performing an explicit flow computation in that region of the vessel.

Figure 3:
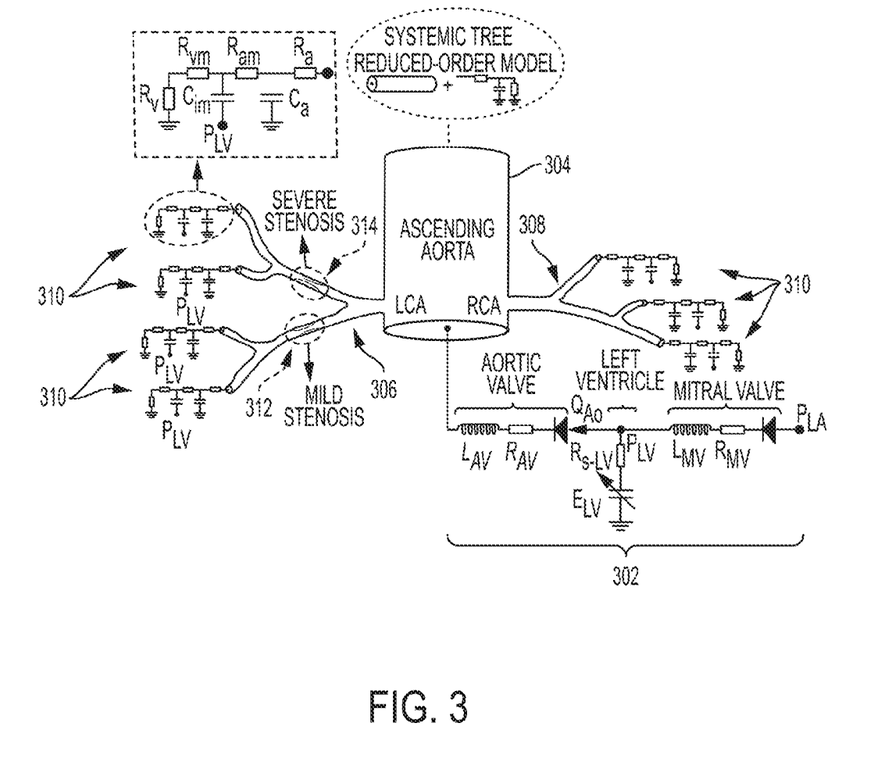
FIG. 3 illustrates an exemplary multi-scale computational model of coronary circulation according to an embodiment of the present invention.

FIG. 3 illustrates an exemplary multi-scale computational model of coronary circulation according to an embodiment of the present invention. As shown in FIG. 3, a heart model 302 is coupled at the root of the aorta. The heart model 302 may be implemented as a lumped model parameterized through patient-specific data as shown in FIG. 3, or may be implemented as a full 3D heart model. Large arteries, such as the aorta 304 together with the large arteries supplied by the aorta (e.g., subclavian, brachiocephalic, common carotid, etc.), the left coronary artery (LCA) 306, and the right coronary artery (RCA) 308 can be represented as 1D blood flow models or full 3D models. Furthermore, semi-analytical circulatory models can be used either separately for certain arterial segments, or embedded within the 1D or 3D models. The vessel walls can be modeled as a purely elastic or visco-elastic material. The wall properties may be determined through an empirical relationship fit to measured data or based on patient-specific estimations of wall compliance. In the model of coronary arterial circulation of FIG. 3, all microvascular beds are simulated through lumped parameter models 310 which account for the resistance applied to the blood flow and for the compliance of the distal vessels. The coronary vascular bed is modeled through such lumped parameter models 310, which are adapted to the coronary circulation in the sense that they take into account the effects of the myocardial contraction on the flow waveform. Stenosis segments 312 and 314 (i.e., regions in the vessels where a stenosis or a narrowing is detected) are shown in the model of coronary arterial circulation. The stenosis segments 312 and 314 cannot be simulated using the 1D blood flow models since there is a high variation in cross-sectional area and the shape of the stenosis influences the blood flow behavior and especially the trans-stenotic pressure drop which plays a major role in the assessment of the functional importance of such a stenosis. According to an advantageous embodiment of the present invention, reduced-order (as compared to a full 3D model) pressure-drop model can be used for each stenosis segment 312 and 314. Additional details regarding the multi-scale computational model of coronary circulation, as well as calculating rest-state and hyperemia-state boundary conditions for the blood flow and pressure computations, are described in United States Patent Publication No. 2013/0132054, entitled "Method and System for Multi-Scale Anatomical and Functional Modeling of Coronary Circulation," United States Patent Publication No. 2013/0246034, entitled "Method and System for Non-Invasive Functional Assessment of Coronary Artery Stenosis," and United States Patent Publication No. 2014/00058715, entitled "Method and System for Non-Invasive Functional Assessment of Coronary Artery Stenosis," and U.S. application Ser. No. 14/689,083, entitled "Method and System for Non-Invasive Computation of Hemodynamic Indices for Coronary Artery Stenosis," which are incorporated herein in their entirety by reference.

As described above, a pressure-drop model can be used to compute the pressure-drop across each stenosis region (e.g., 312 and 314 of FIG. 3) in the pre-stenting anatomical model of the coronary arteries without performing an explicit flow computation in the stenosis region. Various pressure-drop models can be used. For example, the pressure-drop model for a stenosis may be a fully analytical model or may be a model that includes a combination of analytical and empirical terms. A pressure-drop model that includes a combination of analytical and empirical terms is referred to herein as a "semi-empirical pressure-drop model". Other pressure-drop models may be used as well, such as a machine-learning based pressure-drop model that is trained using a machine-learning algorithm to map anatomical and flow features derived from a stenosis to a pressure-drop associated with the stenosis.

In another possible embodiment, the hemodynamic metric, such as FFR, can be calculated automatically based on patient-specific measurements extracted from the medical image data and patient-specific clinical measurements (e.g., heart rate, blood pressure, etc.) acquired for the patient using a machine learning based technique. Details of such machine learning based techniques for calculating FFR are described in U.S. Published Patent Application 2015/0112182, entitled "Method and System for Machine Learning Based Assessment of Fractional Flow Reserve", which is incorporated herein by reference in its entirety.

Once a FFR value (or other hemodynamic metric) is calculated for each stenotic lesion, the FFR value is compared to a threshold vale to determine if the stenotic lesion is hemodynamically relevant. For example, a threshold of 0.8 may be used for FFR, but the present invention is not limited thereto. If the FFR value at a particular stenotic lesion is less than the threshold value (e.g., <0.8), that stenotic lesion is hemodynamically relevant and is included in the plurality of hemodynamically relevant stenotic lesions to be considered for stenting. In addition, for each stenosis region having an FFR value less than the threshold, all preceding stenotic lesions (i.e., in the proximal direction) in a blood flow path in the coronary artery tree may also be identified as hemodynamically relevant stenotic lesions to be considered for stenting.

Returning to FIG. 1, at step 108, a set of treatment options are generated for stenting the stenotic lesions. According to an advantageous implementation, the set of treatment options can be automatically generated. A plurality of treatment options corresponding to a plurality of stent combinations can be generated for each set of hemodynamically relevant stenotic lesions in a particular blood flow path in the coronary artery tree, where each stenting strategy corresponds to stenting a subset of the hemodynamically relevant stenotic lesions. The set of stent combinations can include options corresponding stenting each individual lesion and options corresponding to stenting each possible combination of multiple target stenosis regions, up to an option corresponding to stenting all of the target stenosis regions. In a possible embodiment, multiple treatment options corresponding to different stent characteristics (e.g., implant sizes and/or implant typed, etc.) can be generated for each possible stent combination.

A plurality of stenting options is generated and evaluated (step 110) for a set of lesions that are located in a particular blood flow path in the coronary artery tree. Placing a stent in one of those stenotic lesions impacts the blood flow through and hence the pressure drop across the other lesions downstream and upstream of that lesion. A possible therapeutic goal can be to restore blood flow to a sufficient level (e.g., FFR greater than the threshold value) with a minimum number of stents. The stenting of lesions that are located in separate branches of the coronary tree are treated independently as such lesions have significantly smaller influence. Accordingly, steps 108-114 can be performed independently for each set of lesions in each branch or blood flow path in the coronary arteries.

With two lesions "in series" upstream/downstream of each other, the stenting options are (1) stent lesion #1, (2) stent lesion #2, (3) stent both lesions #1 and #2, and (4) don't stent any lesion. Stenting all lesions (option 3) will restore maximal blood flow. Apart from very pathologic cases, this option can be considered to be curative and, in a possible implementation, does not require extra confirmation by simulation. The evaluation of the stenting options to predict FFR values is performed to determine whether stenting only a subset of the serial lesions is sufficient to restore blood flow such that the predicted FFR values are above the threshold. For the case of two lesions, the evaluation in step 110 can automatically determine whether it is sufficient to stent only lesion #1 or only lesion #2, and if stenting sufficient restores the blood flow, whether lesion #1 or lesion #2 is the preferred lesion to stent. In a possible implementation, we have three stenting options (1)-(3), two of which need to be evaluated. Option (4) can be evaluated by assessing the FFR value after the most distal lesion (in this case downstream of lesion #2) without any stenting. If the FFR value is greater than the threshold (e.g., >0.8), then stenting is not needed for either of the lesions.

In the case of three or more serial lesions, more stenting options are generated and evaluated. For example, in the case of three serial lesions. In particular all stenting options in which a single one of the lesions and all stenting options in which possible combinations of two of the lesions are evaluated. Again, in a possible implementation, the "stent all the lesions" option may not be evaluated and can be accepted as the natural fall back for the case in which none of the stenting options of stenting a subset of lesions restores sufficient blood flow.

At step 110, predicted hemodynamic metrics are automatically computed for each of the treatment options. In an advantageous implementation, a predicted FFR value is computed for each of the stenotic lesions for each of the treatment options. The method of FIG. 1 is described using FFR as the hemodynamic metric. However, the method is not limited thereto and other hemodynamic metrics, such as instantaneous wave-free ratio (iFR) and rest Pd/Pa, may be used as well. In a possible embodiment, the predicted FFR values for a particular treatment option are calculated by adjusting the pressure drop across the stented lesion(s) for that treatment option and then performing a computational fluid dynamics simulation for the remaining vessel tree. For example, the pressure drop for the stented lesion(s) can be set to zero or can be set to a small value to account for the case in which the stenosis may not be opened completely with a stent. Such a small value can be a predetermined value, such as a value derived from results of past therapies, or can be estimated based on a prediction of how successful the stenting of the particular stenosis will be. For example, a machine learning based method can be used to detect calcifications at the stenotic lesion and the prediction of how successful the stenting will be can be estimated based on the amount of calcifications detected. In another possible implementation, the pressure drop of the stented lesion(s) can be adjusted by adjusting the pressure drop model using the method described in U.S. patent application Ser. No. 14/704,233, entitled "Method and System for Prediction of Post-Stenting Hemodynamic Metrics for Treatment Planning of Arterial Stenosis", filed May 5, 2015, which is incorporated herein by reference in its entirety. Once the pressure drop is adjusted for the stented lesion(s), the blood flow simulation is performed and FFR is calculated for each stenotic lesion based on the simulated blood flow and pressure. The blood flow simulation can be performed using CFD using the computational model of coronary circulation as described above in connection with FIG. 3.

FFR is defined as the ratio of the maximal blood flow in the stenotic vessel to the maximal blood flow in a normal vessel, and is used to characterize the severity of the stenosis. FFR can be approximated for a stenosis by calculating the ratio of the time-averaged pressure distal to the stenosis (Pd) with respect to the average pressure in the aorta (Pa) at the hyperemic state. Accordingly, in an advantageous embodiment, the blow flow simulation simulates hyperemic blood flow, and the computed pressure drop for each stenosis can be averaged over a heart cycle and subsequently used to determine the predicted FFR value for each stenosis. In particular, FFR can be computed as $(Pa-\Delta P)/Pa$, where Pa is the aortic pressure and $\Delta P$ is the pressure drop over the stenosis. The aortic pressure may be assumed at a population average value or may be determined as a function of the non-invasively acquired systolic and diastolic pressures, and the heart rate.

In another embodiment, instead of adjusting the pressure drop for the stented lesion(s), the patient-specific anatomical model of the coronary arteries can be automatically or interactively adjusted to include a 3D geometric model of the stented lesion(s) to account for the virtual stenting. For example, the influence of the stent can be applied to the anatomical model by widening the stenosis region to a healthy vessel radius, or if the stent does not open the vessel completely, by widening the anatomical model to a predetermined percentage (e.g., 90%) of a healthy vessel radius. CFD simulations can then be performed using the modified anatomical model of the coronary arteries and FFR values calculated based on the simulations.

In another possible embodiment, the predicted FFR values for each treatment option can be computed by adjusting patient-specific measurements (e.g., radius measurements) for the stented lesion(s) to reflect full or partial opening due to the virtual stenting and then computed FFR values based on the adjusted patient-specific measurements using a machine learning based technique. Details of such machine learning based techniques for calculating FFR are described in U.S. Published Patent Application 2015/0112182, entitled "Method and System for Machine Learning Based Assessment of Fractional Flow Reserve", which is incorporated herein by reference in its entirety.

At step 112, the treatment options are automatically ranked based on the predicted hemodynamic metrics calculated for each treatment option. In an advantageous embodiment, the ranking is based on the predicted FFR values of the lesions for each treatment option as well as the number of stents used in each treatment option. For example, the treatment options can be ranked in order of maximal blood flow restoration (as measured by the FFR values of the lesions), with options with a smaller number of stents ranked ahead of options with a greater number of stents if the options with the smaller number of stents result in predicted FFR values greater than the threshold for all of the lesions. If a lesser number of stents can be deployed to restore sufficient blood flow, this can save money and reduce the risk associated with additional unnecessary stents. Some lesions may be difficult or even impossible to stent, as is often the case for a stenosis in the left main coronary artery or an ostial stenosis. If the blood flow can be sufficiently restored by stenting some of all of the other lesions, stenting is a viable therapy option, whereas otherwise a coronary bypass surgery may be necessary. The ranking of the treatment options can also consider the difficulty or ease of implementation. For example, the left main coronary artery is short and hence difficult to stent. Even if the best blood flow would result from stenting the left main coronary artery, a clinician may decide to perform a coronary bypass operation instead due to the difficult of stenting the left main coronary artery. However, if the stenting of a distal lesion downstream from the left main coronary artery can restore the blood flow sufficiently (e.g., FFR values greater than the threshold value), this option may be the preferred clinical option even if the maximal blood flow restoration is less than the option in which the left main coronary artery is stented. Accordingly, treatment options in which lesions in certain anatomical regions, such as the left main coronary artery, are stented may be penalized in the ranking.

At step 114, the predicted results for the treatment options are displayed. For example, for each of the treatment options for a set of lesions, one or more clinically relevant figure can be generated indicating the merit of the particular treatment option. Such figures can show individual pressure drops and/or FFR values across individual stenotic lesions and/or the compound pressure drops across all the lesions in one path and the corresponding FFR values. These figures can be presented to the user in a way that supports the user in making a therapy decision selecting one of the stenting options. For example, the highest ranked treatment option or top n (e.g., 3) ranked treatment options may be displayed as recommended stenting combinations. A table of results for the various stent configurations that displays the stent configurations in the order of the rankings can be displayed. This may or may not include the "stent all" configuration. In a possible implementation, the results can be color coded such that stent configurations that lead to a sufficient blood flow restoration (e.g., FFR values greater than the threshold value) are displayed in one color and stent configurations that do not result in sufficient blood flow restoration are displayed in another color. A figure that shows the stent locations/configurations on a 3D model or a simplified diagram of the coronary tree can be generated for each treatment option. Pressure drop and/or FFR values for the various lesions can be included in this figure. The respective figures for each of the stent configurations can be displayed side by side or only the stent configurations resulting in sufficient blood flow restoration may be displayed. The figures or merits for the various treatment options can be generated automatically and presented in an overview of results for decision support. A clinical report summarizing all or a subset of the treatment options together with supplemental information, such as images corresponding to the treatment options, may be generated.

In a possible embodiment, the results can be displayed by displaying an enlarged model of the coronary vessel tree (showing the real patient-specific geometry or a simplified diagram), which can be animated such that in response to the user selection of a table entry from the table of possible treatment options, the corresponding stent configuration and FFR/pressure drop results are displayed in the model of the coronary vessel tree "on demand". It is also possible that the user can select locations on the displayed model of the coronary vessel tree to place stents at those locations and the pressure drop and/or FFR values corresponding to the treatment scenario selected by the user can be displayed on the model or highlighted in the table of results. In these embodiments, the results for all of the treatment options can be automatically calculated and stored and then displayed to the user "on demand" in response to a user selection. In this case, the method of FIG. 1 may be partitioned into automatic/off-line calculations and interactive/on-line presentations to the user for review and decision support. Alternatively, with a fast computational method, such as the machine learning based implementation, the "on demand" results may not require pre-calculation and the results can be calculated on demand.

Figure 4:
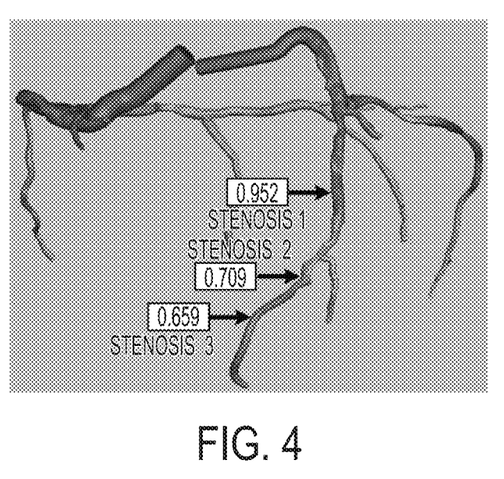
FIGS. 4-10 illustrate predicted FFR values for a set of serial stenotic lesions for different stenting configurations.
Figure 5:
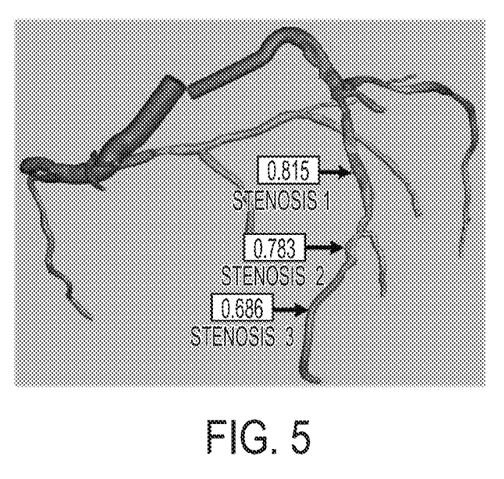
Figure 6:
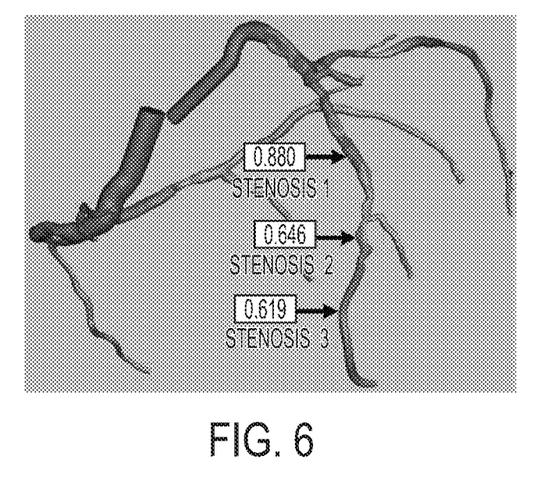
Figure 7:
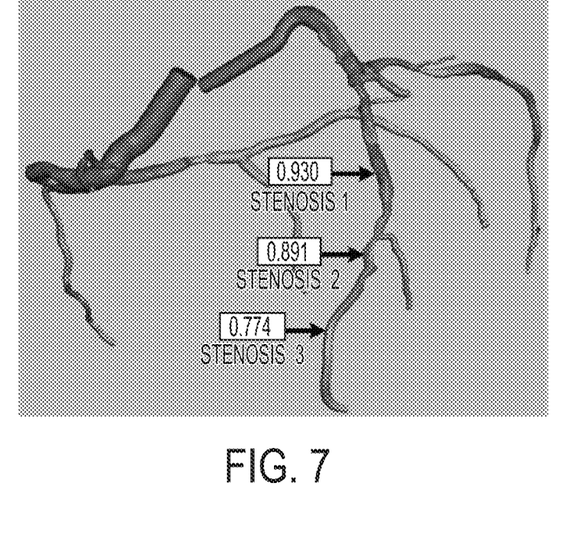
Figure 8:
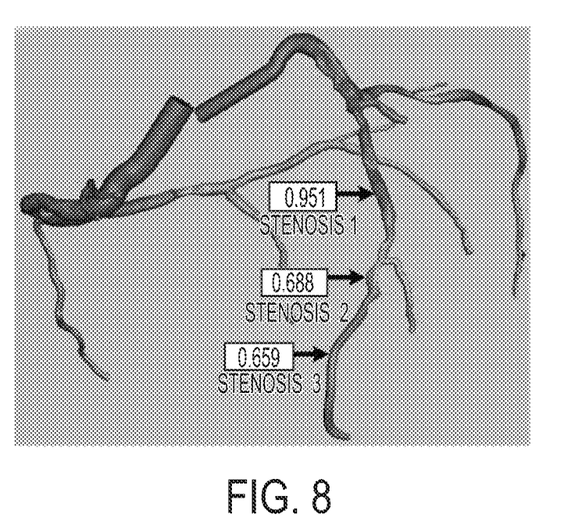
Figure 9:
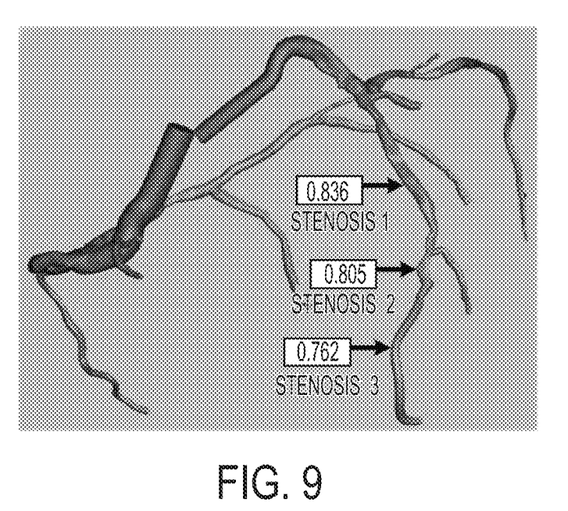
Figure 10:
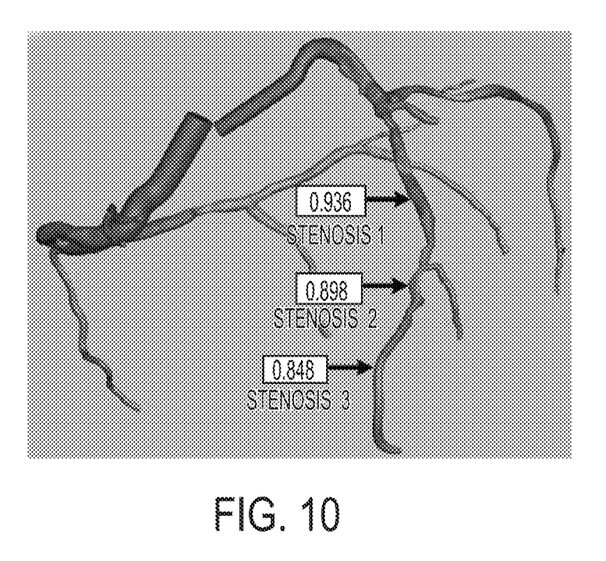

FIGS. 4-10 illustrate predicted FFR values for a set of serial stenotic lesions (stenosis 1, stenosis 2, and stenosis 3) in the left anterior descending (LAD) artery for different stenting configurations. FIG. 4 illustrates predicted FFR values resulting from a stenting configuration in which only stenosis 1 is stented. FIG. 5 illustrates predicted FFR values resulting a stenting configuration in which only stenosis 2 is stented. FIG. 6 illustrates predicted FFR values resulting from a stenting configuration in which only stenosis 3 is stented. FIG. 7 illustrates predicted FFR values resulting from a stenting configuration in which stenosis 1 and stenosis 2 are stented. FIG. 8 illustrates predicted FFR values resulting from a stenting configuration in which stenosis 1 and stenosis 3 are stented. FIG. 9 illustrates predicted FFR values resulting from a stenting configuration in which stenosis 2 and stenosis 3 are stented. FIG. 10 illustrates predicted FFR values resulting from a stenting configuration in which stenosis 1, stenosis 2, and stenosis 3 are all stented.

Figure 11:
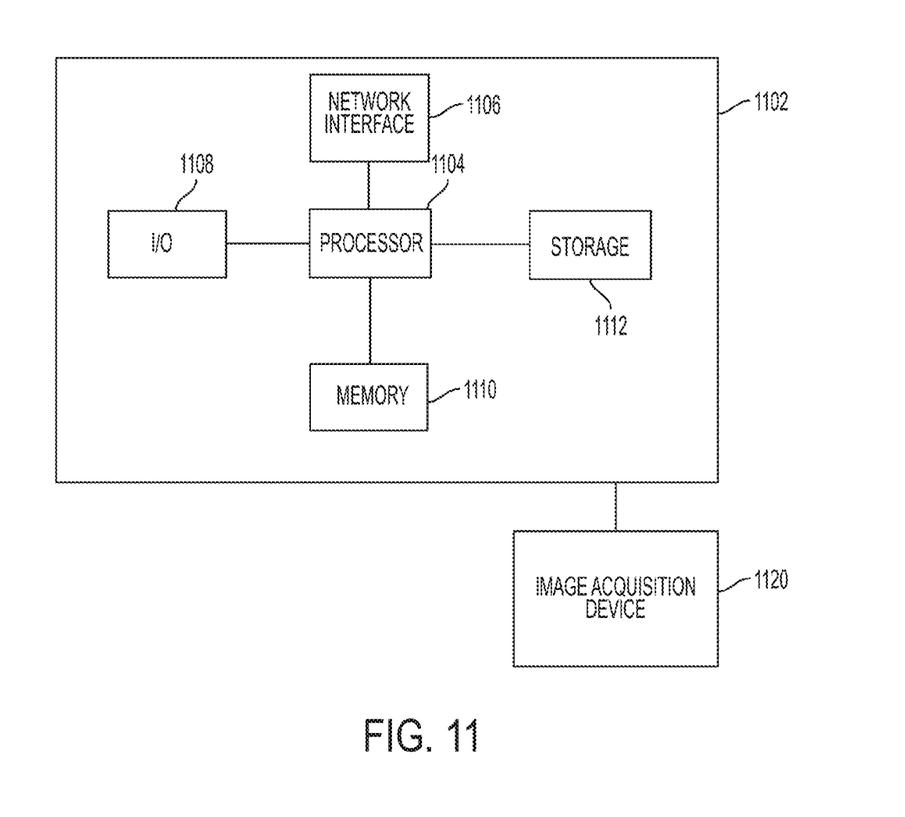
FIG. 11 is a high-level block diagram of a computer capable of implementing the present invention.

The above-described methods for automated decision support for therapy planning for arterial stenoses may be implemented on a computer using well-known computer processors, memory units, storage devices, computer software, and other components. A high-level block diagram of such a computer is illustrated in FIG. 11. Computer 1102 contains a processor 1104, which controls the overall operation of the computer 1102 by executing computer program instructions which define such operation. The computer program instructions may be stored in a storage device 1112 (e.g., magnetic disk) and loaded into memory 1110 when execution of the computer program instructions is desired. Thus, the steps of the methods of FIG. 1 may be defined by the computer program instructions stored in the memory 1110 and/or storage 1112 and controlled by the processor 1104 executing the computer program instructions. An image acquisition device 1120, such as a CT scanning device, MR scanning device, Ultrasound device, etc., can be connected to the computer 1102 to input image data to the computer 1102. It is possible to implement the image acquisition device 1120 and the computer 1102 as one device. It is also possible that the image acquisition device 1120 and the computer 1102 communicate wirelessly through a network. In a possible embodiment, the computer 1102 may be located remotely with respect to the image acquisition device 1120 and the method steps are performed as part of a server or cloud based service. The computer 1102 also includes one or more network interfaces 1106 for communicating with other devices via a network. The computer 1102 also includes other input/output devices 1108 that enable user interaction with the computer 1102 (e.g., display, keyboard, mouse, speakers, buttons, etc.). One skilled in the art will recognize that an implementation of an actual computer could contain other components as well, and that FIG. 11 is a high level representation of some of the components of such a computer for illustrative purposes.

The above-described methods for medical image synthesis may be implemented using computers operating in a client-server relationship. Typically, in such a system, the client computers are located remotely from the server computer and interact via a network. The client-server relationship may be defined and controlled by computer programs running on the respective client and server computers.

The above-described methods for medical image synthesis may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the method steps described herein, including one or more of the steps of FIG. 1. Certain steps of the methods described herein, including one or more of the steps of FIG. 1, may be performed by a server or by another processor in a network-based cloud-computing system. Certain steps of the methods described herein, including one or more of the steps of FIG. 1, may be performed by a client computer in a network-based cloud computing system. The steps of the methods described herein, including one or more of the steps of FIG. 1, may be performed by a server and/or by a client computer in a network-based cloud computing system, in any combination.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for planning treatment for arterial stenotic lesions, comprising:
   identifying a set of stenotic lesions in a patient's coronary arteries from medical image data of the patient;
   generating a plurality of treatment options for the set of stenotic lesions, wherein each of the plurality of treatment options corresponds to a stenting configuration in which one or more of the stenotic lesions are stented;
   calculating, for each of the plurality of treatment options, predicted hemodynamic metrics for the set of stenotic lesions resulting from the stenting configuration corresponding to that treatment option using machine learning or computer based simulation of blood flow and pressure; and
   ranking the plurality of treatment options based on the predicted hemodynamic metrics for the set of stenotic lesions calculated for each of the plurality of treatment options and a number of stents in the stenting configuration corresponding to each of the plurality of treatment options.

2. The method of claim 1, wherein ranking the plurality of treatment options based on the predicted hemodynamic metrics for the set of stenotic lesions calculated for each of the plurality of treatment options and a number of stents in the stenting configuration corresponding to each of the plurality of treatment options comprises:
   ranking the plurality of treatment options in order of maximal blood flow restoration based on the predicted hemodynamic metrics calculated for the set of stenotic lesions, with treatment options having stenting configurations with a smaller number of stents ranked ahead of treatment options having stenting configurations with a larger number of stents if the predicted hemodynamic metrics calculated for the treatment options having the stenting configurations with the smaller number of stents indicate that a blood flow is sufficiently restored.

3. The method of claim 1, wherein ranking the plurality of treatment options based on the predicted hemodynamic metrics for the set of stenotic lesions calculated for each of the plurality of treatment options and a number of stents in the stenting configuration corresponding to each of the plurality of treatment options comprises:
   ranking the plurality of treatment options based on the predicted hemodynamic metrics for the set of stenotic lesions calculated for each of the plurality of treatment options with treatment options having stenting configurations in which a stenotic lesion in a predetermined anatomical region is stented being penalized.

4. The method of claim 1, wherein calculating, for each of the plurality of treatment options, predicted hemodynamic metrics for the set of stenotic lesions resulting from the stenting configuration corresponding to that treatment option comprises:
   calculating, for each of the plurality of treatment options, predicted fractional flow reserve (FFR) values for the set of stenotic lesions resulting from the stenting configuration corresponding to that treatment option.

5. The method of claim 4, wherein calculating, for each of the plurality of treatment options, predicted fractional flow reserve (FFR) values for the set of stenotic lesions resulting from the stenting configuration corresponding to that treatment option comprises:

adjusting a pressure drop simulated for the one or more of the stenotic lesions that are stented in the corresponding stenting configuration;

simulating blood flow and pressure in the coronary arteries of the patient with the adjusted pressure drop for the one or more of the stenotic lesions that are stented; and calculating FFR values for each of the set of stenotic lesions based on the simulated blood flow and pressure in the coronary arteries of the patient.

6. The method of claim 5, wherein adjusting a pressure drop simulated for the one or more of the stenotic lesions that are stented in the corresponding stenting configuration comprises:

adjusting the pressure drop simulated for the one or more of the stenotic lesions that are stented in the corresponding stenting configuration to a pressure drop of zero.

7. The method of claim 5, wherein adjusting a pressure drop simulated for the one or more of the stenotic lesions that are stented in the corresponding stenting configuration comprises:

adjusting the pressure drop simulated for the one or more of the stenotic lesions that are stented in the corresponding stenting configuration to a predetermined value representing partial opening of the one or more stenotic lesions that are stented.

8. The method of claim 1, wherein the plurality of treatment options comprises a respective treatment option corresponding to each possible stenting configuration of one or more of the set of stenotic lesions.

9. The method of claim 1, further comprising:

displaying, for each of the plurality of treatment options, a respective figure showing results of calculating the predicted hemodynamic metrics for the set of stenotic lesions resulting from the stenting configuration corresponding to that treatment option.

10. The method of claim 1, further comprising:

displaying a table of results of calculating the predicted hemodynamic metrics for the set of stenotic lesions resulting from the stenting configuration corresponding to each of the plurality of treatment options in order of the ranking of the plurality of treatment options.

11. The method of claim 1, further comprising:

displaying a model of the patient's coronary arteries; and in response to a user selecting an entry corresponding to a treatment option in a table of treatment options, displaying the stenting configuration corresponding to the selected treatment option and the hemodynamic metrics calculated for the set of stenotic lesions resulting from the stenting configuration corresponding to the selected treatment option.

12. The method of claim 1, further comprising:

displaying a model of the patient's coronary arteries; and in response to a user selection of one or more stent locations on the model of the patient's coronary arteries, displaying the hemodynamic metrics calculated for the set of stenotic lesions for a treatment option corresponding to the stenting configuration indicated by the user selection of the one or more stent locations.

13. The method of claim 1, wherein identifying a set of stenotic lesions in a patient's coronary arteries from medical image data of the patient comprises:

extracting a patient-specific anatomical model of the coronary arteries from the medical image data;

detecting a plurality of stenotic lesions in the coronary arteries using the patient-specific anatomical model of the coronary arteries;

estimating a hemodynamic metric for each of the plurality of stenotic lesions; and identifying a set of hemodynamically relevant stenotic lesions from the plurality of stenotic lesions based on the hemodynamic metric estimated for each of the plurality of stenotic lesions.

14. The method of claim 13, wherein estimating a hemodynamic metric for each of the plurality of stenotic lesions comprises:

simulating blood flow and pressure in the coronary arteries using a computational model of coronary circulation; and estimating the hemodynamic metric for each of the plurality of stenotic lesions based on a simulated pressure drop over each of the plurality of stenotic lesions.

15. The method of claim 13, wherein estimating a hemodynamic metric for each of the plurality of stenotic lesions comprises:

estimating a fractional flow reserve (FFR) value for each of the plurality of stenotic lesions.

16. An apparatus for planning treatment for arterial stenotic lesions, comprising:

means for identifying a set of stenotic lesions in a patient's coronary arteries from medical image data of the patient;

means for generating a plurality of treatment options for the set of stenotic lesions, wherein each of the plurality of treatment options corresponds to a stenting configuration in which one or more of the stenotic lesions are stented;

means for calculating, for each of the plurality of treatment options, predicted hemodynamic metrics for the set of stenotic lesions resulting from the stenting configuration corresponding to that treatment option; and means for ranking the plurality of treatment options based on the predicted hemodynamic metrics for the set of stenotic lesions calculated for each of the plurality of treatment options and a number of stents in the stenting configuration corresponding to each of the plurality of treatment options.

17. The apparatus of claim 16, wherein the means for calculating, for each of the plurality of treatment options, predicted hemodynamic metrics for the set of stenotic lesions resulting from the stenting configuration corresponding to that treatment option comprises:

means for calculating, for each of the plurality of treatment options, predicted fractional flow reserve (FFR) values for the set of stenotic lesions resulting from the stenting configuration corresponding to that treatment option.

18. The apparatus of claim 17, wherein the means for calculating, for each of the plurality of treatment options, predicted fractional flow reserve (FFR) values for the set of stenotic lesions resulting from the stenting configuration corresponding to that treatment option comprises:

means for adjusting a pressure drop simulated for the one or more of the stenotic lesions that are stented in the corresponding stenting configuration;

means for simulating blood flow and pressure in the coronary arteries of the patient with the adjusted pressure drop for the one or more of the stenotic lesions that are stented; and means for calculating FFR values for each of the set of stenotic lesions based on the simulated blood flow and pressure in the coronary arteries of the patient.

19. The apparatus of claim 16, wherein the plurality of treatment options comprises a respective treatment option corresponding to each possible stenting configuration of one or more of the set of stenotic lesions.

20. The apparatus of claim 16, further comprising:
means for displaying, for each of the plurality of treatment options, a respective figure showing results of calculating the predicted hemodynamic metrics for the set of stenotic lesions resulting from the stenting configuration corresponding to that treatment option.

21. The apparatus of claim 16, further comprising:
means for displaying a table of results of calculating the predicted hemodynamic metrics for the set of stenotic lesions resulting from the stenting configuration corresponding to each of the plurality of treatment options in order of the ranking of the plurality of treatment options.

22. The apparatus of claim 16, wherein the means for identifying a set of stenotic lesions in a patient's coronary arteries from medical image data of the patient comprises:
means for extracting a patient-specific anatomical model of the coronary arteries from the medical image data;
means for detecting a plurality of stenotic lesions in the coronary arteries using the patient-specific anatomical model of the coronary arteries;
means for estimating a hemodynamic metric for each of the plurality of stenotic lesions; and
means for identifying a set of hemodynamically relevant stenotic lesions from the plurality of stenotic lesions based on the hemodynamic metric estimated for each of the plurality of stenotic lesions.

23. A non-transitory computer readable medium storing computer program instructions for planning treatment for arterial stenotic lesions, the computer program instructions when executed by a processor causes the processor to perform operations comprising:
identifying a set of stenotic lesions in a patient's coronary arteries from medical image data of the patient;
generating a plurality of treatment options for the set of stenotic lesions, wherein each of the plurality of treatment options corresponds to a stenting configuration in which one or more of the stenotic lesions are stented;
calculating, for each of the plurality of treatment options, predicted hemodynamic metrics for the set of stenotic lesions resulting from the stenting configuration corresponding to that treatment option using machine learning or computer based simulation of blood flow and pressure; and
ranking the plurality of treatment options based on the predicted hemodynamic metrics for the set of stenotic lesions calculated for each of the plurality of treatment options and a number of stents in the stenting configuration corresponding to each of the plurality of treatment options.

24. The non-transitory computer readable medium of claim 23, wherein calculating, for each of the plurality of treatment options, predicted hemodynamic metrics for the set of stenotic lesions resulting from the stenting configuration corresponding to that treatment option comprises:
calculating, for each of the plurality of treatment options, predicted fractional flow reserve (FFR) values for the set of stenotic lesions resulting from the stenting configuration corresponding to that treatment option.

25. The non-transitory computer readable medium of claim 24, wherein calculating, for each of the plurality of treatment options, predicted fractional flow reserve (FFR) values for the set of stenotic lesions resulting from the stenting configuration corresponding to that treatment option comprises:
adjusting a pressure drop simulated for the one or more of the stenotic lesions that are stented in the corresponding stenting configuration;
simulating blood flow and pressure in the coronary arteries of the patient with the adjusted pressure drop for the one or more of the stenotic lesions that are stented; and
calculating FFR values for each of the set of stenotic lesions based on the simulated blood flow and pressure in the coronary arteries of the patient.

26. The non-transitory computer readable medium of claim 23, wherein the plurality of treatment options comprises a respective treatment option corresponding to each possible stenting configuration of one or more of the set of stenotic lesions.

27. The non-transitory computer readable medium of claim 23, wherein the operations further comprise:
displaying, for each of the plurality of treatment options, a respective figure showing results of calculating the predicted hemodynamic metrics for the set of stenotic lesions resulting from the stenting configuration corresponding to that treatment option.

28. The non-transitory computer readable medium of claim 23, wherein the operations further comprise:
displaying a table of results of calculating the predicted hemodynamic metrics for the set of stenotic lesions resulting from the stenting configuration corresponding to each of the plurality of treatment options in order of the ranking of the plurality of treatment options.

29. The non-transitory computer readable medium of claim 23, wherein the operations further comprise:
displaying a model of the patient's coronary arteries; and
in response to a user selecting an entry corresponding to a treatment option in a table of treatment options, displaying the stenting configuration corresponding to the selected treatment option and the hemodynamic metrics calculated for the set of stenotic lesions resulting from the stenting configuration corresponding to the selected treatment option.

30. The non-transitory computer readable medium of claim 23, wherein the operations further comprise:
displaying a model of the patient's coronary arteries; and
in response to a user selection of one or more stent locations on the model of the patient's coronary arteries, displaying the hemodynamic metrics calculated for the set of stenotic lesions for a treatment option corresponding to the stenting configuration indicated by the user selection of the one or more stent locations.

31. The non-transitory computer readable medium of claim 23, wherein identifying a set of stenotic lesions in a patient's coronary arteries from medical image data of the patient comprises:
extracting a patient-specific anatomical model of the coronary arteries from the medical image data;
detecting a plurality of stenotic lesions in the coronary arteries using the patient-specific anatomical model of the coronary arteries;
estimating a hemodynamic metric for each of the plurality of stenotic lesions; and
identifying a set of hemodynamically relevant stenotic lesions from the plurality of stenotic lesions based on the hemodynamic metric estimated for each of the plurality of stenotic lesions.

32. The non-transitory computer readable medium of claim 31, wherein estimating a hemodynamic metric for each of the plurality of stenotic lesions comprises:

simulating blood flow and pressure in the coronary arteries using a computational model of coronary circulation; and estimating the hemodynamic metric for each of the plurality of stenotic lesions based on a simulated pressure drop over each of the plurality of stenotic lesions.

33. The non-transitory computer readable medium of claim 31, wherein estimating a hemodynamic metric for each of the plurality of stenotic lesions comprises:

estimating a fractional flow reserve (FFR) value for each of the plurality of stenotic lesions.

* * * * *